(12) United States Patent
Das et al.

(10) Patent No.: US 10,716,501 B2
(45) Date of Patent: Jul. 21, 2020

(54) SYSTEM AND METHOD FOR CLASSIFICATION AND QUANTITATIVE ESTIMATION OF COGNITIVE STRESS

(71) Applicant: Tata Consultancy Services Limited, Mumbai (IN)

(72) Inventors: Deepan Das, Kolkata (IN); Tanuka Bhattacharjee, Kolkata (IN); Shreyasi Datta, Kolkata (IN); Anirban Dutta Choudhury, Kolkata (IN); Pratyusha Das, Kolkata (IN); Arpan Pal, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 315 days.

(21) Appl. No.: 15/913,731

(22) Filed: Mar. 6, 2018

(65) Prior Publication Data
US 2019/0175091 A1    Jun. 13, 2019

(30) Foreign Application Priority Data
Dec. 13, 2017    (IN) .............................. 201721044813

(51) Int. Cl.
*A61B 5/16*    (2006.01)
*A61B 5/0476*    (2006.01)
(Continued)

(52) U.S. Cl.
CPC ............ *A61B 5/165* (2013.01); *A61B 5/0205* (2013.01); *A61B 5/02405* (2013.01);
(Continued)

(58) Field of Classification Search
CPC ... A61B 5/165; A61B 5/02405; A61B 5/7475; A61B 5/0205; A61B 5/048;
(Continued)

(56) References Cited

U.S. PATENT DOCUMENTS

| 2005/0054904 | A1* | 3/2005 | El-Nokaly | A61B 5/16 600/300 |
| 2009/0253982 | A1* | 10/2009 | Wang | A61B 5/055 600/419 |
| 2012/0101346 | A1* | 4/2012 | Scott | A61B 5/1124 600/300 |

OTHER PUBLICATIONS

Alberdi, A. et al. (Feb. 2016). "Towards an automatic early stress recognition system for office environments based on multimodal measurements: A review," *Journal of Biomedical Informatics*, vol. 59; pp. 49-75.

(Continued)

*Primary Examiner* — Lindsey G Wehrheim
(74) *Attorney, Agent, or Firm* — Finnegan, Henderson, Farabow, Garrett & Dunner LLP

(57) ABSTRACT

This disclosure relates generally to stress classification and quantification, and more particularly to system and method for classification and quantitative estimation of cognitive stress from analysis of keystrokes and signals derived from physiological sensors. In one embodiment, a method includes obtaining, while a user is engaged in performance of a task, physiological signals from physiological sensors accessible to the user. Feature sets are identified from the physiological signals which correlate with cognitive stress experienced by the user. Using a regression model, a stress indicator metric comprising a quantitative estimate of the cognitive stress is predicted. The regression model is trained using the feature sets and independently determined quantitative estimates of cognitive stress used as a ground truth to output the value of the stress indicator metric. The ground truth is determined from keystroke data associated with the performance of keyboard-based tasks comprising navigation of moving objects to the target.

17 Claims, 7 Drawing Sheets

(51) Int. Cl.

| | | |
|---|---|---|
| *A61B 5/024* | (2006.01) | |
| *A61B 5/053* | (2006.01) | |
| *G16H 50/20* | (2018.01) | |
| *A61B 5/11* | (2006.01) | |
| *A61B 5/00* | (2006.01) | |
| *G06N 5/02* | (2006.01) | |
| *G06N 20/00* | (2019.01) | |
| *A61B 5/0205* | (2006.01) | |
| *A61B 5/048* | (2006.01) | |

(52) U.S. Cl.
CPC .......... *A61B 5/02416* (2013.01); *A61B 5/048* (2013.01); *A61B 5/0476* (2013.01); *A61B 5/0533* (2013.01); *A61B 5/1123* (2013.01); *A61B 5/7203* (2013.01); *A61B 5/7207* (2013.01); *A61B 5/7267* (2013.01); *A61B 5/7475* (2013.01); *G06N 5/022* (2013.01); *G06N 20/00* (2019.01); *G16H 50/20* (2018.01); *A61B 5/7435* (2013.01); *A61B 2503/12* (2013.01)

(58) Field of Classification Search
CPC . A61B 5/7203; A61B 5/0476; A61B 5/02416; A61B 5/0533; A61B 5/1123; A61B 5/7207; A61B 5/7267; A61B 2503/12; A61B 5/7435; G06N 20/00; G06N 5/022; G16H 50/20
See application file for complete search history.

(56) References Cited

OTHER PUBLICATIONS

Singh, R.R. et al. (Oct. 2014). "Assessment of Driver Stress from Physiological Signals collected under Real-Time Semi-Urban Driving Scenarios," *International Journal of Computational Intelligence Systems*, vol. 7, No. 5; pp. 909-923.

Gunawardhane, S. et al. "Non Invasive Human Stress Detection Using Key Stroke Dynamics and Pattern Variations," *2013 International Conference on Advances in ICT for Emerging Regions (ICTer)*, Colombo, Sri Lanka, Dec. 11-15, 2013; 8 pages.

Ang, K.K. et al. (Mar. 2012). "Filter bank common spatial pattern algorithm on BCI competition IV Datasets 2a and 2b," *Frontiers in Neuroscience*, vol. 6, No. 39; pp. 1-9.

\* cited by examiner

SYSTEM AND METHOD FOR CLASSIFICATION AND QUANTITATIVE ESTIMATION OF COGNITIVE STRESS

PRIORITY CLAIM

This U.S. patent application claims priority under 35 U.S.C. § 119 to: India Application No. 201721044813, filed on Dec. 13, 2017. The entire contents of the aforementioned application are incorporated herein by reference.

TECHNICAL FIELD

This disclosure relates generally to stress classification and quantification, and more particularly to system and method for classification and quantitative estimation of cognitive stress from analysis of keystrokes and signals derived from physiological sensors.

BACKGROUND

Stress is the response of the human body subjected to an unfavorable stimulus. Acute stress is the effect of short term perturbing situations, often manifested by temporary changes in physiological variables. Acute stress for longer periods of time can lead to episodic stress. Even longer exposure to stress elements or traumatic conditions can lead to chronic stress, anxiety or clinical depression. According to World health organization (WHO), loss of productivity at work as well as treatment of mental health related problems cost large amounts of money worldwide. Hence detection of early symptoms of stress can assist in preserving the mental wellbeing of a large section of the vulnerable population.

There have been various methods and systems that are conventionally designed to simulate stressful conditions for determining behavioral and cognitive stress of humans. The inventors have recognized certain technical problems associated with currently available solutions pertaining to stress estimation and/or prediction as explained below. For example, typical stress estimation methods and systems use self-reporting of stress as the ground truth for comparison. However, said methods can be highly biased, may include false reporting and are inherently person-dependent. In addition, said methods are mostly found to be lacking a continuous metric for stress indication throughout a stress estimation session.

SUMMARY

Embodiments of the present disclosure present technological improvements as solutions to one or more of the above-mentioned technical problems recognized by the inventors in conventional systems. For example, in one embodiment, a processor-implemented method for classification and quantitative estimation of cognitive stress in real-time. The method includes obtaining, while a user is engaged in performance of a task, a plurality of non-invasive physiological signals from a plurality of physiological sensors accessible to the user, via one or more hardware processors. Further the method includes identifying a plurality of feature sets from the plurality of non-invasive physiological signals, via the one or more hardware processors, the plurality of feature sets correlating with the cognitive stress experienced by the user while engaging in the performance of the task. Furthermore the method includes predicting, using a regression model, a stress indicator metric comprising a quantitative estimate of the cognitive stress experienced by the user during the performance of the task, via the one or more hardware processors. Herein, the regression model is trained using the plurality of feature sets and independently determined quantitative estimates of cognitive stress used as a ground truth to output the value of the stress indicator metric. The ground truth is determined from keystroke data associated with the performance of keyboard-based tasks comprising navigation of one or more moving objects to at least one target from a plurality of targets.

In another embodiment, a system for classification and quantitative estimation of cognitive stress in real-time is provided. The system includes one or more memories; and one or more hardware processors, the one or more memories coupled to the one or more hardware processors, wherein the one or more hardware processors are capable of executing programmed instructions stored in the one or more memories to obtain, while a user is engaged in performance of a task, a plurality of non-invasive physiological signals from a plurality of physiological sensors accessible to the user. Further, the one or more hardware processors are configured by the instructions to identify a plurality of feature sets from the plurality of non-invasive physiological signals, the plurality of feature sets correlating with the cognitive stress experienced by the user while engaging in the performance of the task. Furthermore, the one or more hardware processors are configured by the instructions to predicting, using a regression model, a stress indicator metric comprising a quantitative estimate of the cognitive stress experienced by the user during the performance of the task, via the one or more hardware processors. Herein, the regression model is trained using the plurality of feature sets and independently determined quantitative estimates of cognitive stress used as a ground truth to output the value of the stress indicator metric. The ground truth is determined from keystroke data associated with the performance of keyboard-based tasks comprising navigation of one or more moving objects to at least one target from a plurality of targets.

In yet another embodiment, a non-transitory computer-readable medium having embodied thereon a computer program for executing a method for classification and quantitative estimation of cognitive stress in real-time. The method includes obtaining, while a user is engaged in performance of a task, a plurality of non-invasive physiological signals from a plurality of physiological sensors accessible to the user. Further, the method includes identifying a plurality of feature sets from the plurality of non-invasive physiological signals, the plurality of feature sets correlating with the cognitive stress experienced by the user while engaging in the performance of the task. Furthermore the method includes predicting, using a regression model, a stress indicator metric comprising a quantitative estimate of the cognitive stress experienced by the user during the performance of the task, via the one or more hardware processors. Herein, the regression model is trained using the plurality of feature sets and independently determined quantitative estimates of cognitive stress used as a ground truth to output the value of the stress indicator metric. The ground truth is determined from keystroke data associated with the performance of keyboard-based tasks comprising navigation of one or more moving objects to at least one target from a plurality of targets.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1A:
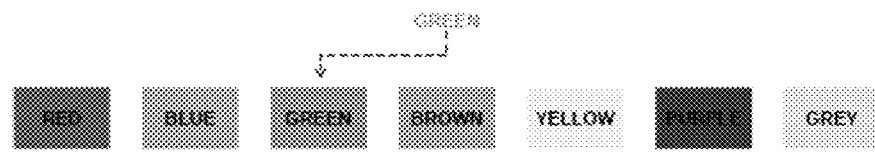
FIGS. 1A and 1B illustrate example versions of a specific keyboard based task for classification and quantification of cognitive stress according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Stress is one of a major cause of concern in today's world. Stress is the response of the human body subjected to an unfavorable stimulus. Acute stress is the effect of short term perturbing situations, often manifested by temporary changes in physiological variables of a user under stress. Acute stress for longer periods of time can lead to episodic stress. Even longer exposure to stress elements or traumatic conditions can lead to chronic stress, anxiety or clinical depression.

Conventionally, various models have been designed in prior arts to simulate stressful conditions for studying behavioral and cognitive stress of humans. The Stroop test is such a well-known psychological test. Similarly, the Tetris game has also been known to elicit cognitive load.

Traditionally, physiological signals are considered as a viable choice for analyzing and monitoring the level of stress experienced by an individual. In a traditional experiment for monitoring the stress level, three different levels of stress were induced, namely low, medium and high, on a driver, when he took rest and drove through a highway and a city road respectively. Said experiment empirically showed GSR and Heart Rate Variability (HRV) measures to be the best indicators for real-time stress-level monitoring. In another experiment attempted to identify stress in computer users using the 'Paced Stroop Test', GSR and Blood Volume Pulse (BVP) are employed among other signals. In yet another experiment, the stress dynamics of an examinee is analyzed during an multiple choice question (MCQ) test by means of Galvanic Skin Response (GSR) and Photoplethysmogram (PPG) signals. They used a scoring mechanism based on fluctuation analysis of GSR to estimate the level of stress perceived. HRV was found to be informative about the guess work done during the test. Yet another set of experiments were conducted with controlled stressors under laboratory conditions. Low stress sessions required the participants to key in numbers, displayed on-screen, with encouragement from a friendly instructor. The high stress sessions added a memory task along with elements of socio-evaluative threat, by recording the sessions and portraying a neutral instructor. Features obtained from HRV and continuous blood pressure, were determined to correlate to the self-reported stress levels of individuals.

Certain other conventional works concerned with correlating Electroencephalography (EEG) patterns to stress are less abundant. For example, discrete cosine transform (DCT) coefficients of a single-lead EEG recording were made while the participants were being administered the Stroop Color-Word Interference test. On the basis of self-reported stress, participants could be categorized into stressed and non-stressed groups. On reducing it to a 2-class classification problem, the features performed well in conjunction with KNN classification. In another similar work, EEG features were found to correlate more highly with trends in varying self-reported stress than either HRV (from ECG) or GSR.

However, the inventors have recognized certain technical problems associated with currently available solutions pertaining to stress estimation and/or prediction as explained below. For example, most of the conventional techniques use self-reporting of stress as the ground truth for comparison. Therefore, said methods can be highly biased, may include false reporting and are inherently person-dependent. Further, most of the approaches have not explored fusion of multiple sensor data that may lead to higher performance. Additionally, the conventional techniques and/or experiments for stress determination are mostly lacking a continuous metric for stress indication throughout an experimental session.

Various embodiments presented herein disclose system and method for classification and quantification of cognitive stress from physiological signals and keystrokes. For example, in one embodiment, the system utilizes multiple physiological signals during a specific task to discriminate between high and low cognitive stress. The disclosed system is further capable of determining a stress indicator metric, from a keystroke analysis performed during a specific keyboard based task, to provide a quantitative estimate of cognitive stress perceived by an individual, and train a person-dependent regression model using features derived from physiological signals only to predict the same metric. An example of said specific task is described with reference to FIGS. 1A and 1B.

Figure 1B:
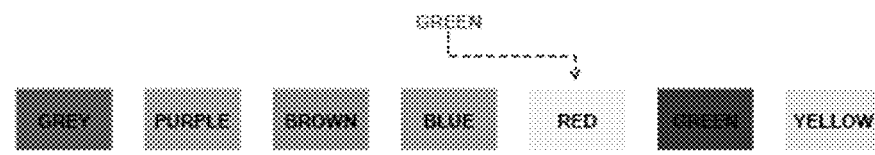

Referring to FIGS. 1A and 1B, versions of a specific task for classification and quantification of cognitive stress are illustrated. In an embodiment, said specific task is a keyboard-based task. The keyboard-based task includes navigation of one or more moving objects to at least one target from a plurality of targets. In an embodiment, said keyboard based task may include using for navigation of the moving objects. It will be understood that herein the specific task is described to include a keyboard based task as described above. In alternate embodiments, however, the task may include any task being performed by user, for instance, walking, running, climbing stairs, and so on. It will also be understood herein that the herein the target includes a single target only, however, in alternate embodiments the target may include more than one target so as to induce varying levels of the stress in the player/participant. Further, in case there is only one target object, the moving objects may be navigated by using dedicated keys, for example, a right hand key and a left hand key. However, in case of multiple target objects, the navigation may be performed by various keys or other means of navigation such as gestures, joystick, and so on. The details of an example scenario pertaining to keyboard based tasks are explained hereinunder by taking reference of a Stroop Tetris game.

The purpose of the keyboard based task by using the Stroop Tetris game is to induce two distinctly different levels of cognitive stress in the participants. The conventional experiments and/or techniques have often used different arithmetic tasks, of varying difficulty, for the same purpose. However, individual difference in ability causes very different levels of stress to be induced by such tasks, even in the presence of socio-evaluative threat. In this respect, in an example scenario of the disclosed method and system, a gamified version of the Stroop Colour-Word test is considered a more universal stressor for the subjects who possessed adequate familiarity with English names of colours, adequate proficiency in reading and writing in English and faced no difficulty in colour perception.

In an example embodiment, the Stroop test is gamified using elements of the popular Tetris game. As illustrated in FIGS. 1A and 1B, the gameplay screens include two difficulty levels, along with the correct choice to be made. While engaging in the game, the participants may be required to direct the text, descending at constant speed, to the correct bin using only left and right arrow keys. It may be assumed that the subjects are proficient in the use of a computer with a standard QWERTY keyboard.

In the easy version (refer, FIG. 1A) of the game, the text colour matches the text name, the bin colour matches the bin name. So the correct choice is obvious and creates low cognitive stress in the participants. In the difficult version (refer, FIG. 1B), the text colour does not match the text name, as is with the bin colour and the bin name. The player must match the bin name to the text colour. This double occurrence of colour-word mismatch may be introduced so that the players may be unable to match word-to-word or colour-to-colour. Accordingly, as described with reference to FIGS. 1A and 1B, the example Stroop Tetris test may be utilized for inducing varying levels of cognitive stress in participants, and while the participant is engaged in playing the game, the cognitive stress experienced by the user may be recorded (by using various sensors communicably coupled to the participant). Said sensors may output physiological signals that can be analysed for determining the cognitive stress experienced by the user under varying stress conditions. The description herein provides method and system for classification and quantitative estimation of cognitive stress from physiological signals and keystrokes.

The methods and systems are not limited to the specific embodiments described herein. In addition, the method and system can be practiced independently and separately from other modules and methods described herein. Each device element and/or module and method can be used in combination with other elements/modules and other methods.

The manner, in which the system and method classification and quantification of cognitive stress shall be implemented, has been explained in details with respect to the FIGS. 2 through 10C. While aspects of described methods and systems for classification and quantification of cognitive stress can be implemented in any number of different systems, utility environments, and/or configurations, the embodiments are described in the context of the following exemplary system(s).

Figure 2:
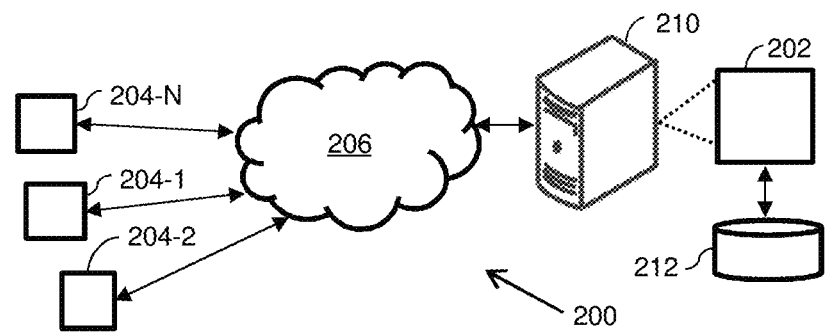
FIG. 2 illustrates a network implementation of a system for classification and quantification of cognitive stress according to some embodiments of the present disclosure.

Referring now to FIG. 2, a network implementation 200 of system 202 for classification and quantification of cognitive stress is illustrated, in accordance with an embodiment of the present subject matter. The system is adapted to classify cognitive stress, at an inter-personal level, induced by a performance of a task. The system 202 captures signal information including information gathered from Electroencephalogram (EEG) signal, Galvanic Skin Response (GSR) signal and Photoplethysmogram (PPG) signal using for example, a wearable device such as a smart watch being worn by the subject. Features are derived from each sensors are aimed at discriminating low and high cognitive stress, followed by feature reduction. In addition, the system is capable of determining a stress indicator metric derived from the keystrokes of the subjects to quantify real-time value of cognitive stress.

Although the present subject matter is explained considering that the system 202 is implemented for classification and quantification of cognitive stress, it may be understood that the system 202 may not be restricted to any particular machine or environment. The system 202 may be implemented in a variety of computing systems, such as a laptop computer, a desktop computer, a notebook, a workstation, a mainframe computer, a server, a network server, a smart phone, a wearable device, and the like.

The system 202 may acquire an input data while the user (or subject) is engaged in performance of a task, via devices and/or machines 204-1, 204-2 . . . 204-N, collectively referred to as devices 204 hereinafter. Herein, the task may be a keyboard based task or a non-keyboard based task, as explained with reference to FIG. 1A, 1B. In an embodiment, the devices 204 may include, but are not limited to a wearable device for example, a smart watch. In an embodiment, the devices 204 may be embodied in handheld electronic device, a mobile phone, a smartphone, a portable computer, a PDA, and so on. The devices 204 are communicatively coupled to the system 202 through a network 206, and may be capable of providing input data to the system 202.

In one implementation, the network 206 may be a wireless network, a wired network or a combination thereof. The network 306 can be implemented as one of the different types of networks, such as intranet, local area network (LAN), wide area network (WAN), the internet, and the like. The network 206 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 206 may include a variety of network devices, including routers, bridges, servers, computing devices, storage devices, and the like.

In an embodiment, the system 202 may be embodied in the computing device 210. The system 202 may also be associated with a data repository 212 to store data associated with the classification and quantification of cognitive stress. Additionally or alternatively, the data repository 212 may be configured to store data and/or information generated during classification and quantification of cognitive stress. The repository 212 may be configured outside and communicably coupled to the computing device 210 embodying the system 202. Alternatively, the data repository 212 may be configured within the system 202. An example implementation of the system 202 for classification and quantification of cognitive stress is described further with reference to FIG. 3.

Figure 3:
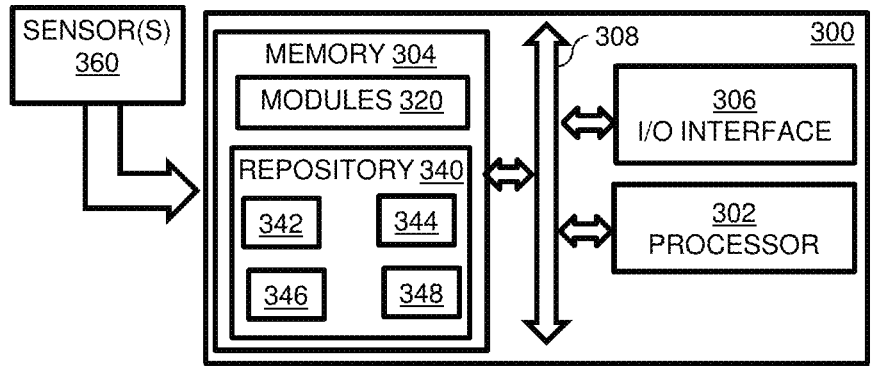
FIG. 3 illustrates a block diagram of a system for classification and quantification of cognitive stress in accordance with some embodiments of the present disclosure.

FIG. 3 illustrates a block diagram of an exemplary system 300 for classification and quantification of cognitive stress, in accordance with an example embodiment. The system 300 may be an example of the system 202 (FIG. 2). In an example embodiment, the system 300 may be embodied in, or is in direct communication with the system, for example the system 202 (FIG. 2). The system 300 includes or is otherwise in communication with one or more hardware processors such as a processor 302, at least one memory such as a memory 304, and an I/O interface 306. The processor 302, memory 304, and the I/O interface 306 may be coupled by a system bus such as a system bus 308 or a similar mechanism.

The hardware processor 302 may include circuitry implementing, among others, audio and logic functions associated with the communication. For example, the processor 302 may include, but are not limited to, one or more digital signal processors (DSPs), one or more microprocessor, one or more special-purpose computer chips, one or more field-programmable gate arrays (FPGAs), one or more application-specific integrated circuits (ASICs), one or more computer(s), various analog to digital converters, digital to analog converters, and/or other support circuits. The processor 302 thus may also include the functionality to encode messages and/or data or information. The processor 302 may include, among other things, a clock, an arithmetic logic unit (ALU) and logic gates configured to support operation of the processor 302. Further, the processor 302 may include functionality to execute one or more software programs, which may be stored in the memory 304 or otherwise accessible to the processor 302. The hardware processor 302 may be implemented as one or more microprocessors, microcomputers, microcontrollers, digital signal processors, central processing units, state machines, logic circuitries, and/or any devices that manipulate signals based on operational instructions. Among other capabilities, the processor 302 is configured to fetch and execute computer-readable instructions stored in the memory 304.

The I/O interface 306 may include a variety of software and hardware interfaces, for example, a web interface, a graphical user interface, and the like The interfaces 306 may include a variety of software and hardware interfaces, for example, interfaces for peripheral device(s), such as a keyboard, a mouse, an external memory, a camera device, and a printer. Further, the interfaces 306 may enable the system 302 to communicate with other devices, such as web servers and external databases. The interfaces 306 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 306 may include one or more ports for connecting a number of computing systems with one another or to another server computer. The I/O interface 306 may include one or more ports for connecting a number of devices to one another or to another server.

The memory 304 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 304 includes a plurality of modules 320 and a repository 340 for storing data processed, received, and generated by one or more of the modules 320. The modules 320 may include routines, programs, objects, components, data structures, and so on, which perform particular tasks or implement particular abstract data types. Additionally, the other modules 320 may include programs or coded instructions that supplement applications and functions of the system 300. The repository 340, amongst other things, includes a system database 342 and other data 344. The other data 344 may include data generated as a result of the execution of one or more modules in the modules 320. Herein, the memory for example the memory 304 and the computer program code configured to, with the hardware processor for example the processor 302, causes the system 300 to perform various functions described herein under. Additionally, the repository 340 may include a sensor data 346 and a keystroke data 348. The sensor data 346 may be obtained from one or more sensors 360 employed for physiological sensing of a subject/player. The sensor data 346 may include PPG signals obtained classification and quantitative estimation of cognitive stress. The keystroke data 348 may be obtained upon execution of keyboard based tasks by the users/participants/players. The details of the sensor data and the keystroke data are explained further in the description below.

In an embodiment, the system 300 obtains, while a user is engaged in performance of the task, a plurality of non-invasive physiological signals from physiological sensors accessible to the user. Said physiological sensor may be embodied in at least one wearable device such as the device 204 (FIG. 2) accessible to or worn by the user. Herein, the plurality of non-invasive physiological signals includes, but are not limited to, Electroencephalogram (EEG) signal to estimate the neural responses of the user, Photoplethysmogram (PPG) signal to analyze the variations in heart rate and other cardiac parameters of the user, as well as the Electrodermal or Galvanic Skin Response (GSR) changes of the user due to variations in skin conductance; with and without the occurrence of stressors. It will be understood that multiple physiological signals can provide insights into the mental state of an individual.

The system 300 develops a classification model to differentiate between high and low cognitive stress experienced by an individual, from the plurality of non-invasive physiological signals. In an embodiment, the classification model includes a regression model, as will be explained later in the description. The regression model developed herein is robust with respect to sensors and readily deployable, without further training, on any new data available from a new subject.

Herein, the physiological signals obtained from the device(s) 204 may be corrupted due to noise, thereby leading to intra-subject and inter-subject variability and increased computational effort of subsequent processes. In order to reduce the noise in the physiological signals, the system 300 is caused to preprocess the physiological signals individually. In an embodiment, the system 204 preprocesses the plurality of non-invasive physiological signals in order to reduce corruption of the plurality of non-invasive physiological by noise, reduce intra-user and inter-user variability and decrease computational effort for identifying the plurality of feature steps and predicting the stress indicator metric. In an example embodiment, the EEG signals may be preprocessed by a Muse device that is capable of measuring brain activity via multiple EEG sensors. The Muse device may internally applies a 50 Hz notch filter on data obtained at each channel from the EEG sensors in order to eliminate power line interference. For instance, power supply frequency in India is 50 Hz. Since the signal analysis involves frequency components up to the gamma band which is typically most apparent at 40 Hz, the signal at each channel is passed through a 6th order elliptical low-pass filter having the cut-off frequency of 45 Hz. In the next step, the median value of the rest segment is subtracted from both the rest and activity data segments to eliminate the DC bias present. Here, for the purpose of normalization, an inter quartile range has been used, instead of range, because of its robustness against outliers.

For the purpose of preprocessing the GSR signals, the raw skin resistance signal, in kΩ, obtained from Shimmer, is first converted to conductance in μSiemens. This signal is low-pass filtered by a 32nd order FIR constrained equi-ripple filter with cut-off frequency of 0.4 Hz. Finally, the signal is normalized by subtracting the minimum value of the initial rest period signal and dividing by the range of the same.

In order to preprocess the PPG signal, each PPG data segment associated with the PPG is first converted to a zero-mean signal by subtracting the mean of that signal from each sample. It is then bandpass filtered in the frequency range of [0.75 15] Hz to remove high frequency noise. Zero phase forward and reverse digital filtering with an 80th order FIR filter, designed using the Hamming window, is employed for this purpose. To model the baseline of the PPG signal, a piecewise third order polynomial is fitted through the signal troughs. This baseline is then removed from the entire data segment. Herein, the plurality of non-invasive physiological signals have been preprocessed, as described above. However, for the sake of brevity of description, said preprocessed signals will be referred to as physiological signals.

The system 300 identifies a plurality of feature sets from the plurality of non-invasive physiological signals. In an embodiment, the system 300 identifies the plurality of feature sets by extracting a feature set individually from each non-invasive physiological signal of the plurality of non-invasive signals to obtain the plurality of feature sets. For example, for extraction of a feature set from the EEG signals, raw signals from each of the 4 channels of the Muse device can be analysed separately. STFT, with 256 samples per window and an overlap of 234 samples, may be performed on each channel to obtain time series of power contained in $\delta$, $\theta$, $\alpha$, $\beta$, and $\gamma$ bands. These may be re-referenced by subtracting the median power of the corresponding band from the rest state EEG. Finally, statistical parameters like median, standard deviation, skewness, kurtosis, minimum and maximum may be determined from the resulting time series. Similar parameters may also computed for EEG asymmetry, where EEG asymmetry is defined as a difference of logarithm of power between left and right channels for each of frontal and parietal locations in each frequency band. Additional features computed extracted from the EEG signal may include three Hjorth parameters.

For extraction of feature set from the GSR signal, ratio of median values during rest state and task state of the user may be considered for both tonic and phasic power. An orienting response may be considered as significant if its trough-to-peak height is at least 0.05 μSiemens. Morphological features may include number of orienting responses and median of orienting response height, rise time, AUC under rising part as in, half-recovery time as in as well as the kurtosis of the orienting response. All morphological features may be derived from GSR signal during task only. Other features may include DFA slope, mean power during task and ratio of fluctuation index during task and rest.

In order to extract features from PPG signal, several HRV related and other time-domain features obtained from the PPG signal may be considered. In order to calculate said features, at first, the NN interval time-series was derived from the PPG signal. Then the mean, standard deviation, mean-absolute-deviation and Shannon entropy of the NN intervals, normalized RMSSD, SDSD, pNN50 and pNN20 may be extracted. The median of the heart rate derived from the PPG signal may also be considered as a time-domain feature. The frequency-domain PPG features involves the normalized spectral power of the NN interval time-series in the frequency bands of 0-0.04 Hz, 0.04-0.15 Hz, 0.15-0.5 Hz, 0.5-0.75 Hz and 0.75-1 Hz. The pairwise ratios of these normalized spectral powers may also be considered. The morphological PPG features includes mean, median and standard deviation of each of normalized systolic time, normalized diastolic time, ratio of systolic and diastolic time and cardiac cycle length; median of the pulse height, rising slope, falling slope, ratio of the rising and falling slope, area under the curve for the systolic and diastolic part of the cardiac cycle, ratio of these two areas, ratio of the slopes in systole, ratio of the slopes in diastole, pulse width at 25%, 33%, 50% and 75% of the pulse height as well as the pairwise ratios of these pulse widths.

Once the system 300 extracts all the features sets related to each of the particular signal modality, for example, from each of the physiological signal, the system assesses relative merits of said features sets by applying a feature reduction method. In an embodiment, the system 300 performs feature reduction on each feature set of the plurality of feature sets to obtain an optimum feature set that minimizes computational demand and maximizes performance. In an embodiment, the system 300 performs the feature reduction using maximizing relevance minimum redundancy (mRMR). The mRMR method performs the feature ranking by maximizing the relevance of a feature with the class labels while minimizing the redundancy among the feature set. Said ranking may be performed individually on the plurality of feature sets obtained from EEG, GSR and PPG.

The plurality of feature sets identified from the physiological signals correlates with the cognitive stress experienced by the user while engaging in the performance of the task. In an embodiment, the system 300 predicts a stress indicator metric comprising a quantitative estimate of the cognitive stress experienced during the performance of the task. The system 300 predicts the stress indicator metric (S) using a regression model that is trained using the plurality of feature sets and independently determined quantitative estimates of cognitive stress used as a ground truth to output the value of the stress indicator metric.

Herein, the ground truth is determined from keystroke data associated with performance of keyboard-based tasks. The keyboard-based tasks may include navigation of one or more moving objects to exactly one target from a plurality of stationary targets using only left and right hand keys. In an embodiment, the keyboard-based tasks may be performed by attempting Versions of Stroop Tetris game, as described with reference to FIGS. 1A, 1B.

In order to estimate the quantitative measure of the cognitive stress from the keystrokes, the system 300 obtains the keystroke data during performance of at least one keyboard-based task. The system determines relative position of the moving object with respect to the ultimate target object during each epoch of the keyboard based task. An epoch associated with the moving object includes a duration of time available for directing said moving object to the target object. Herein, the relative position is determined in terms of keystrokes ($y_s$) made during the performance of keystroke based task in a direction towards the target object and keystrokes ($y_o$) away in a direction away from the target object, such that relative position of the target object is $x=y_s-y_o$. The system 300 defines, for each of the epochs during the keyboard-based task, a single value of f(t) at each time instant (t=0 to T, T=duration of epoch) timestamp is logged such that:

$f(t)=f(t-1)$ denotes no keystroke at time $t$, $f(t)=f(t-1)-1-x$ denotes 1 keystroke in opposite direction at time $t$, and $f(t)=f(t-1)+1+x$ denotes 1 keystroke in same direction as $x$ at time $t$.

The stress metric indicator S=(A−10B)/T−0.5, where A represents rewards for persistence and B represents penalties for indecision. The factor of 10 is introduced to increase penalty on indecisive movements during keyboard based task.

Herein, $A=\Sigma_{t=0}^{T}\min[f(T),\max\{f(t),f(0)\}]$ $B=\Sigma_{t=0}^{T}|\min\{f(t),f(0)\}|+\max\{f(t),f(T)\}-f(T)$ Some possible gameplays and the corresponding values of S are shown in FIGS. 6B-6E. Thus, S assumes high (usually positive) values when the subject (while performing the keyboard based task) is relaxed and low (usually negative) values when the subject is stressed. In an embodiment, the lower values of S are clipped at −1. Thus, −1<=S<0.5.

In an embodiment, the system 300 develops a classification model from the plurality of non-invasive physiological signals to differentiate between high and low cognitive stress experienced by the user.

In an embodiment, for developing the classification model, the system 300 classifies the level of cognitive stress based on the plurality of feature sets obtained from the plurality of non-invasive physiological signals using a feature level fusion and a decision level fusion.

In an embodiment, the feature level fusion of the plurality of feature sets includes accumulating the feature sets associated with the plurality of non-invasive physiological signals to obtain a composite feature set. Further the system 300 performs feature reduction of the composite feature set. In an embodiment, the feature reduction of the composite feature set is performed using mRMR. The system performs the decision level fusion by training a plurality of RF classification models individually corresponding to each of the plurality of features set from each non-invasive physiological signals as originating from the high stress or low stress task(s). Further, the system 300 applies a logical AND operator to the binary classification outcome of the plurality of non-invasive physiological signals obtained from the individual classifiers. The output of the classifier upon applying the logical AND operator provides a classification of cognitive stress experienced by the user as high stress or low stress. An example flow-diagram illustrating a processor-implemented method for classification and quantification of cognitive stress is described further with reference to FIG. 4.

Figure 4:
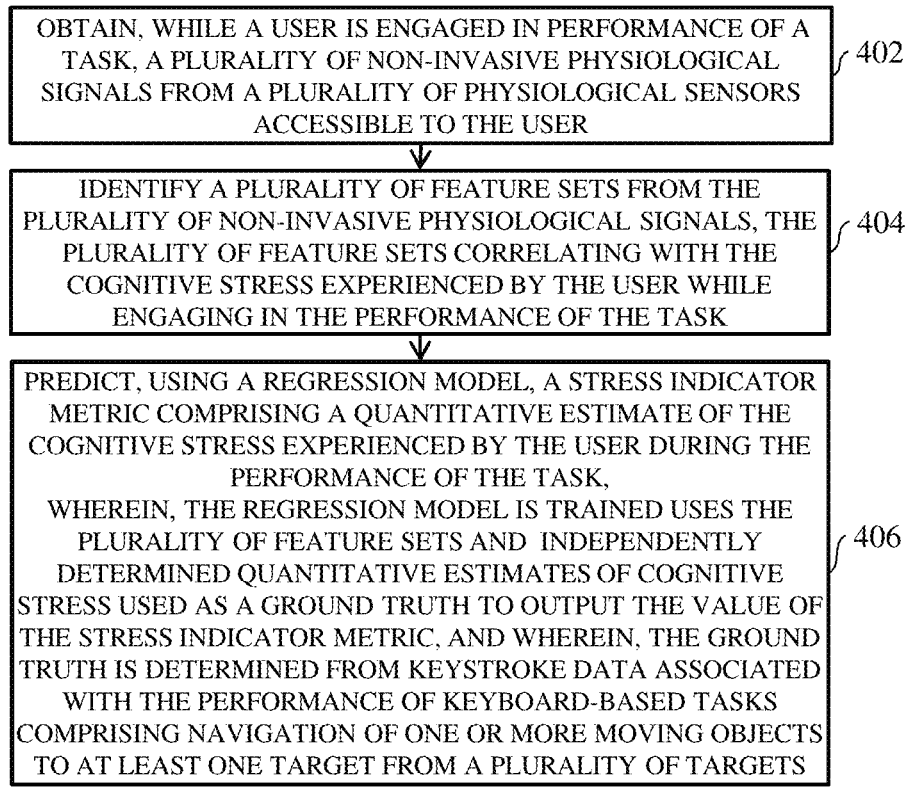
FIG. 4 illustrates an example flow diagram of a method for classification and quantification of cognitive stress in accordance with some embodiments of the present disclosure.

FIG. 4 illustrates a flow diagram of a method 400 for classification and quantification of cognitive stress, according to some embodiments of the present disclosure. The method 400 may be described in the general context of computer executable instructions. Generally, computer executable instructions can include routines, programs, objects, components, data structures, procedures, modules, functions, etc., that perform particular functions or implement particular abstract data types. The method 400 may also be practiced in a distributed computing environment where functions are performed by remote processing devices that are linked through a communication network. The order in which the method 400 is described is not intended to be construed as a limitation, and any number of the described method blocks can be combined in any order to implement the method 400, or an alternative method. Furthermore, the method 400 can be implemented in any suitable hardware, software, firmware, or combination thereof. In an embodiment, the method 400 depicted in the flow chart may be executed by a system, for example, the system 202 of FIG. 2. In an example embodiment, the system 202 may be embodied in an exemplary computer system.

At 402, the method 400 includes obtaining, while a user is engaged in performance of a task, a plurality of non-invasive physiological signals from a plurality of physiological sensors accessible to the user. At 404, the method 400 includes identifying a plurality of feature sets from the plurality of non-invasive physiological signals. The plurality of feature sets correlates with the cognitive stress experienced by the user while engaging in the performance of the task, as is explained with reference to FIG. 3. At 406, the method 400 includes predicting, using a regression model, a stress indicator metric comprising a quantitative estimate of the cognitive stress experienced by the user during the performance of the task. Herein, the regression model is trained using the plurality of feature sets and independently determined quantitative estimates of cognitive stress used as a ground truth to output the value of the stress indicator metric. The ground truth is determined from keystroke data associated with the performance of keyboard-based tasks comprising navigation of one or more moving objects to at least one target from a plurality of targets. An example process flow for classification and quantification of cognitive stress with reference to an example scenario is described further in FIG. 5.

Figure 5:
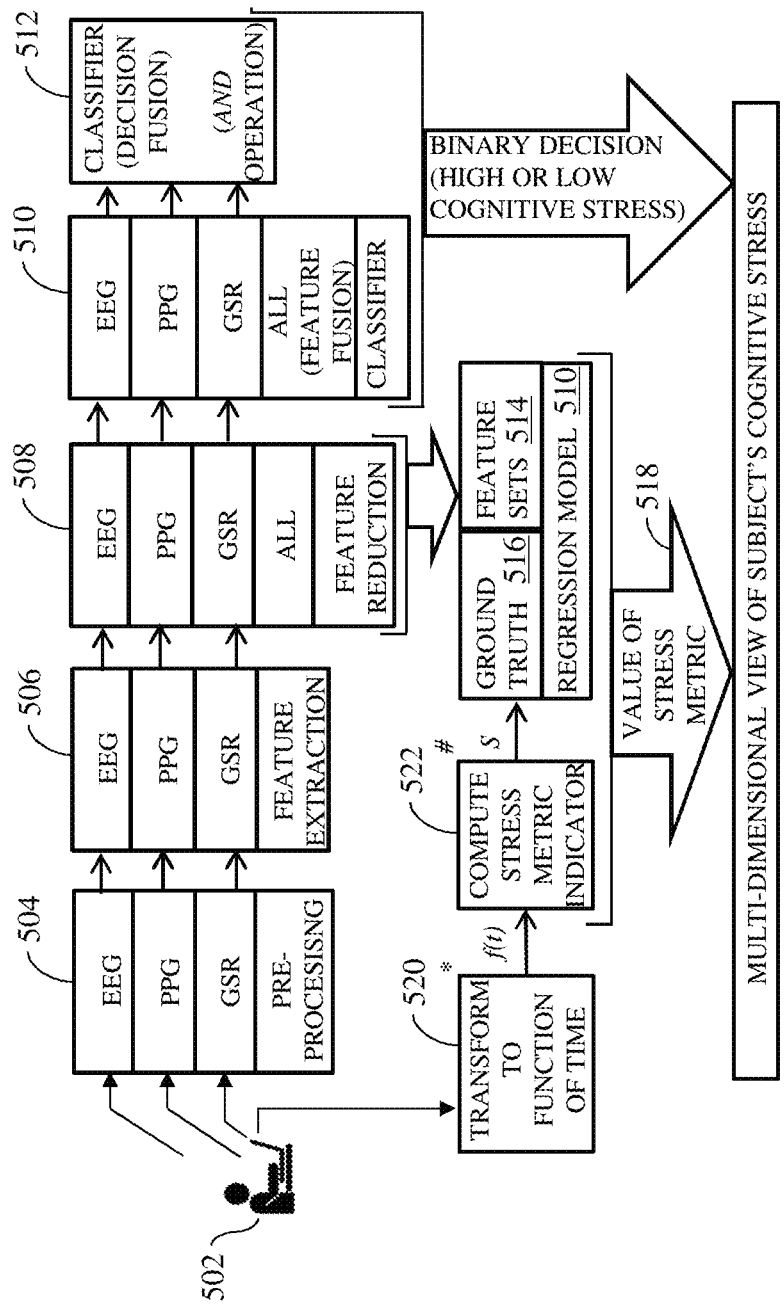
FIG. 5 illustrates example process flow for classification and quantification of cognitive stress in accordance with some embodiments of the present disclosure.

FIG. 5 illustrates an example process flow for classification and quantification of cognitive stress, according to some embodiments of the present disclosure. As illustrated with reference to FIG. 5, a user 502 may perform a task. In an embodiment, the task may be keyboard based task. Alternatively, the task may refer to any physical and/or mental task. Herein, the task may act as a stimulus for inducing cognitive stress in the user 502. It will be noted that for the purpose of designing and training model for cognitive stress estimation, herein the user may be a player of a key board based task. Once the model is designed, it can be utilized directly by a user (wearing a wearable device accommodating the disclosed system) for classification and quantification of the cognitive stress experienced by said user. For the purpose of this description, the terms 'user', 'player' and 'subject' may be used interchangeably.

For the purpose of training the model, the subject may be induced with two levels of cognitive stress, a high level of stress and a low level of stress. In an example scenario, a gamified version of the Stroop Colour-Word test was considered a more universal stressor for the subjects who possessed adequate familiarity with English names of colours, adequate proficiency in reading and writing in English and faced no difficulty in colour perception. The Stroop test may be gamified using elements of the Tetris game, as is described with reference to FIGS. 1A and 1B.

In an example scenario, for the purpose of training the model to design the system, it may be declared that the scores shall be public, although it may not be the case. All participants may be familiar with each other to some extent. No participant may have ever played or observed the game before this experiment. This may ensure that the subjects may be genuinely interested in the game, perceived socio-evaluative threat and tried to maximize their scores. As illustrated in FIGS. 1A and 1B, the gameplay may include difficulty levels, along with the correct choice to be made. Participants may be required to direct the text, descending at constant speed, to the correct bin using only left and right arrow keys. All subjects may be considered to have sufficient computer proficiency with a standard QWERTY keyboard. Score may be displayed on-screen.

In the easy version of the game (FIG. 1A), the text color matches the text name, the bin color matches the bin name. So the correct choice is obvious and creates low cognitive stress. In the difficult version (FIG. 1B), the text color does not match the text name, as is with the bin color and the bin name. The player must match the bin name to the text color. This double occurrence of color-word mismatch may be introduced so that the players would be unable to match word-to-word or color-to-color.

In the experimental set all the subjects/participants undertaking the game may be seated comfortably in a chair in front of a computer in an indoor location with a constant comfortable temperature and constant artificial lighting conditions. Every subject may be allowed to play the game on the same LCD monitor with identical display settings and using the same full-size keyboard, all placed at a comfortable distance and orientation on a table in front. There may not be any distracting elements in the subjects' field of view.

The disclosed system may be caused to collect various non-invasive physiological signals, such as EEG, PPG and GSR from the subjects while the subjects are engaged in the task, for example the Stroop test. For example, GSR may be collected using a single Shimmer 3 GSR+2 unit at 10.2 Hz. Gel-based electrodes may be used instead of the dry electrodes supplied with Shimmer. Electrodes may be placed between the middle and proximal digital creases of the second and third digits of the non-dominant hand. PPG can be collected using the Contec CMS50D+ digital pulse oximeter at 60 Hz, from the second digit of the same hand. EEG can be recorded using the 4-channel Muse 2016 headband at 220 Hz. All devices interfaced with the computer using in-the box software. All devices may be provided with timestamps. Keystroke data including the key strokes during gameplay may be recorded. Subjects' comments regarding difficulty may also be recorded. All data may be anonymized.

Each subject may play the two difficulty levels of the game only once. Instructions for a level may be provided just before the corresponding session for that difficulty level. All devices (incorporating PPG, EEG and GSR sensors) may then started recording the respective physiological signals. The subject may be first instructed to assume a relaxed position in a reclining chair with eyes closed for 60 seconds. After that, the subject may be instructed to sit straight for 10s and stare at a fixation cross on the display. This screen may be replaced by the gameplay screen of the easy version, at which point the subject used only the dominant hand to play using left and right arrow keys. In an example scenario, the may game last for say 110 seconds. Thus, the entire protocol for the easy version may provide 180 (60+10+110) seconds of clearly segmented data. Said protocol may again be observed for the difficult version. Thus, each subject may provide data for 1 easy and 1 difficult session, totaling 360 (2*180) seconds.

The physiological signals such as the EEG, PPG and GSR may be preprocessed at 504, as is explained previously with reference to FIG. 3. Further, feature sets may be extracted individually from the preprocessed physiological signals at 506. Once all the feature sets related to each signal modality are extracted, the relative merits of those features may be assessed by performing feature reduction at 508. In an embedment, feature reduction is performed by mRMR technique. The method performs the feature ranking by maximizing the relevance of a feature with the class labels while minimizing the redundancy among the feature set. This ranking is performed individually on the three feature sets obtained from EEG, GSR and PPG.

At 510, a classification model is developed from the plurality of non-invasive physiological signals to differentiate between high and low cognitive stress experienced by the user. In an embodiment, a Random Forest (RF) model is employed for carrying out the classification between the high and low levels of stress. In the present example scenario, ten differently seeded RFs are used and Leave One Out Cross validation (LOOCV) is performed with respect to subjects in each case. The overall test-set classification accuracies obtained from all these RFs are reported throughout this section. High cognitive stress is considered class 1, hence accuracy in detecting high stress is equivalent to Sensitivity ($S_e$). Likewise, detection accuracy of low cognitive stress is equivalent to Specificity ($S_p$).

Figure 6A:
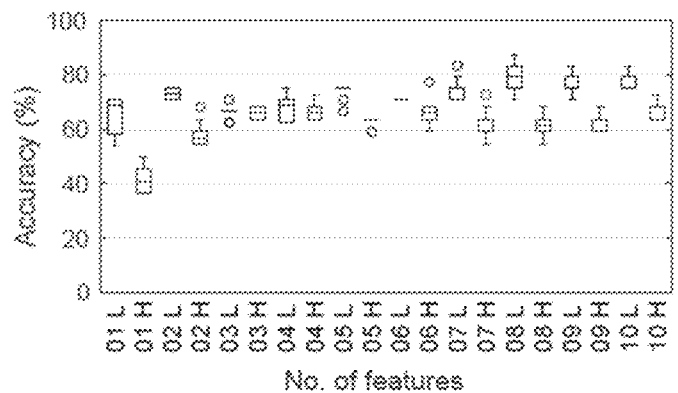
FIGS. 6A-6C illustrates observed performances corresponding to EEG, GSR and PPG signals in accordance with some embodiments of the present disclosure.
Figure 6B:
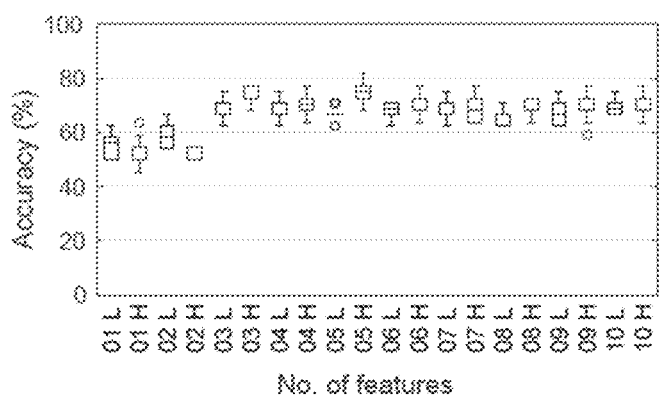
Figure 6C:
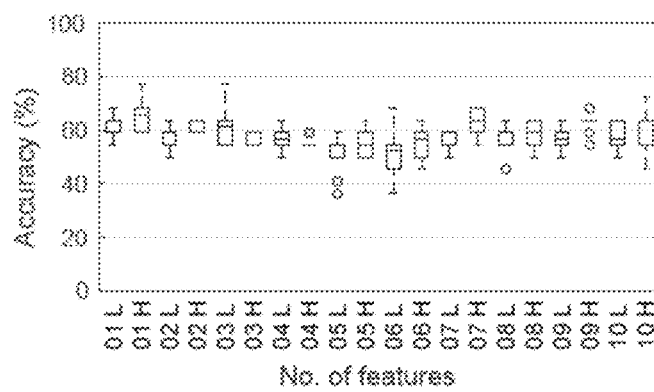

The stress level is classified based on the feature sets obtained from each individual signal modality. FIGS. 6A-6C illustrates observed performances corresponding to EEG, GSR and PPG signals. In each case, the classification accuracy (per class) is plotted against the number of features employed. The features are sequentially added, according to the ranks obtained from mRMR-based feature selection. In case of EEG features (FIG. 6A), the best performance with high accuracy and low difference between the two classes is obtained for the all the top 10 features together. Median and interquartile range of accuracy are respectively 68.2%, [68.2 63.6]% for high-load task while the same are 77.3% and [77.3 72.7]% for low-load task. GSR analysis also yielded highest accuracies for the 10 best features (FIG. 4B). In case of high-load task, GSR features exhibit a median accuracy of 72.7% and interquartile range of [72.7 68.2]% while low-load task show 65.9% and [68.2 63.6]% instead. However, for PPG features, the performance is quite low, as is evident from FIG. 6C. PPG-based classification yields the best results using the top 1 feature only, where median and range for high-load and low-load tasks are respectively 65.9%, [59.1 68.2]%, 63.6% and [59.1 63.6]% classifying the level of cognitive stress based on the plurality of feature sets obtained from the plurality of non-invasive physiological signals using a feature level fusion at 510 and a decision level fusion at 512.

Referring back to FIG. 5, at 510, the classification model classifies level of cognitive stress by combining the information obtained from EEG and GSR. The fusion is performed at two different levels as described next. Herein, in the present example, the PPG based analysis is precluded from fusion because of unsatisfactory performance at individual level. This might be due to the fact that the HRV based features obtained from PPG analysis were not significantly represented within such a small stimulus duration (around 1 min). For feature level fusion at 510, a composite feature set is formed by accumulating all features from EEG and GSR signals, followed by feature reduction.

Figure 7:
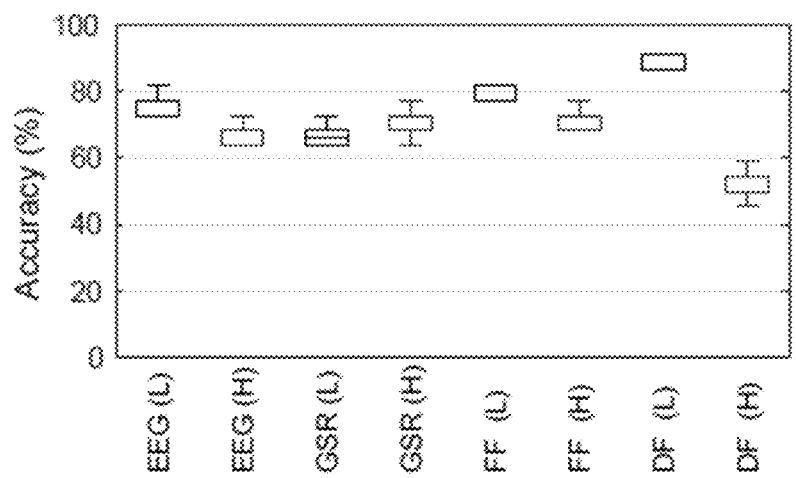
FIG. 7 illustrates classification accuracies for the composite feature set in accordance with some embodiments of the present disclosure.

In order to implement decision level fusion at 512, individual RFs are first trained for each type of sensor signal, and then the inferences obtained from these are combined to reach the final result. This combination operation is performed by taking a logical AND operation on the inferences obtained from the individual RFs. Once again, 10 differently seeded RFs are used for each fold of LOOCV with respect to subjects, followed by selecting the feature set with the best performance for each individual classifier. FIG. 7 depicts the classification accuracies for the composite feature set using LOOCV method. FIG. 7 shows that feature level fusion outperformed decision-level fusion across all test instances (=10 i.e. leave one out×10 RFs in each). Final median accuracies are 81.8% and 72.7% respectively for low-load and high-load tasks, while the interquartile ranges are, in order, [81.8 77.3]% and [72.7 68.2]%.

In an embodiment, a value of a stress indicator metric is predicted using a regression model. The value of a stress indicator metric represents a quantified value or quantitative estimate of the cognitive stress experienced during the performance of the task. The regression model is trained using the plurality of feature sets 514 and independently determined quantitative estimates of cognitive stress used as a ground truth 516 to output the value of the stress indicator metric based on the plurality of feature sets. The ground truth is determined from key-stroke data associated with the performance of keyboard-based tasks, as will be explained in detail below.

The key-stroke data is obtained during the performance of keyboard-based tasks by the user/player. The keyboard-based tasks includes navigation of one or more moving objects to exactly one target from a plurality of stationary targets using only left and right hand keys. In alternate embodiments, the keyboard based tasks may include said navigation to more than one task without restricting to the left/right hand keys, thereby altering the difficulty version of the keyboard based task, and hence altering the level of cognitive stress induced to the player while being engaged in said task.

It will also be understood that there may be participants who, while playing the difficult version of the game, might not have been more stressed than while playing the easy version. Factors like preoccupation, anticipation, novelty, increased sensitivity to socio-evaluative threat etc. may have elevated the stress levels during the easy version. Likewise, familiarizing quickly to the game, absence of perceived socio-evaluative threat, over-explanation by the instructor etc. may have diminished the stress during the difficult version. In such a scenario, the keystroke analysis of the gameplay can reflect exactly how stressed the individual felt during each epoch of the gameplay. Herein, an epoch may be defined as the time duration during which a falling text floated down to the bottom of the screen, which is equal to the total time a player had to direct it to the correct bin.

The players may not always realize whether they were targeting the correct bin or not, until after the epoch when they saw the score being updated. For example, suppose the correct bin was 4 keystrokes to the right, but the player mistakenly believed that the destination was 4 keystrokes to the left (one of the possible errors in the case shown in FIG. 1B). The player played accordingly, never realized the error during that epoch and did not feel stressed. Hence, rather than the position of the correct bin, the intended destination of the player should be used in estimating stress. Moreover, the system must take into account the response time and changes in direction of movement.

Accordingly, in order to estimate a quantitative measure of the cognitive stress from the keystrokes, the keystroke data is obtained during performance of the keyboard-based task and said keyboard based task data is transformed to a function of time at 518. For example, the relative position of the moving object with respect to the ultimate target object is determined during each epoch of the keyboard based task. The relative position is determined in terms of keystrokes ($y_s$) made during the performance of keystroke based task in a direction towards the target object and keystrokes ($y_o$) away in a direction away from the target object, such that relative position of the target object is $x=y_s-y_o$, which reduced to $1=(y_s/x)-(y_o/x)$.

As an example, let the intended destination (also the correct bin) be 4 keystrokes to the right (FIG. 1B). Thus $x=4$. A player pressed the left and right keys in the following order, where each set of keystrokes represents a certain target the player had in mind—4 left (targeting the 3rd bin), 3 left (progressing towards 1st bin, but changing midway), 15 right (targeting the 6th bin), 4 left (targeting the 5th and correct bin). Thus, $y_s=15$ and $y_o=4+3+4$.

Figure 8A:
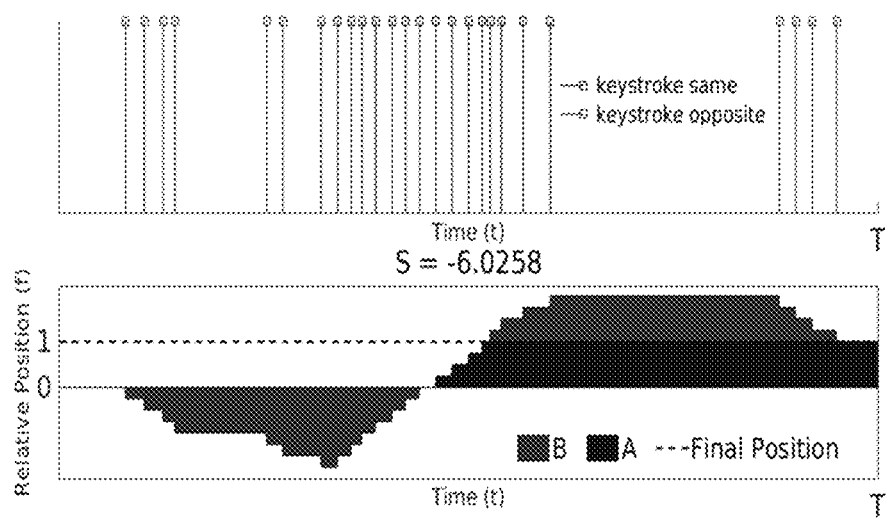
FIG. 8A illustrates an example representation of keystroke data and changes in f, to compute stress indicator metric in accordance with some embodiments of the present disclosure.
Figures 8B, 8C:
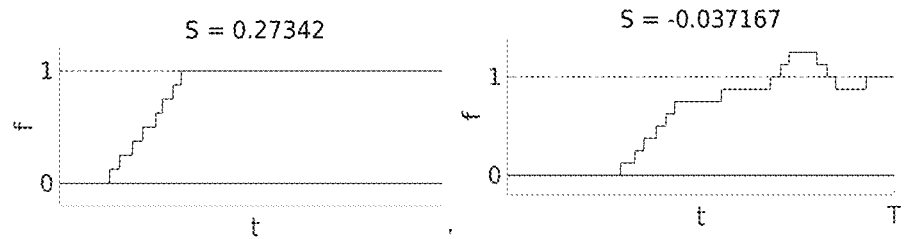
FIGS. 8B-8E illustrates example gameplays and corresponding values of stress indicator metric in accordance with some embodiments of the present disclosure.
Figures 8D, 8E:
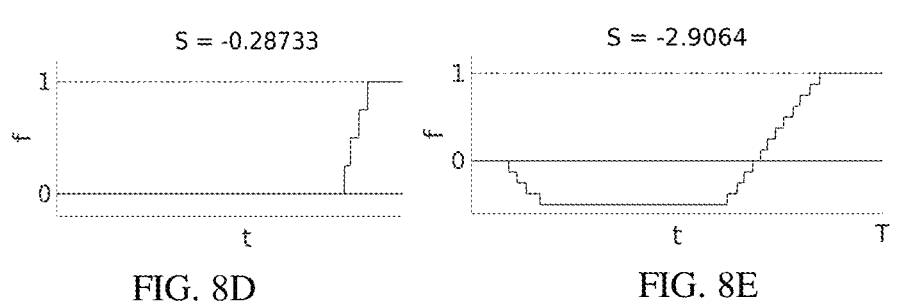

A single value of f(t) is defined for each of the epochs during the keyboard-based task at each time instant (t=0 to T, T=duration of epoch) timestamp is logged, where 1 unit on the horizontal axis denotes the inverse of the frequency at which timestamps for keystrokes are logged such that:

$f(t)=f(t-1)$ denotes no keystroke at time $t$ $f(t)=f(t-1)-1-x$ denotes single keystroke in opposite direction ($y_o$) at time $t$ $f(t)=f(t-1)+1+x$ denotes single keystroke in same direction ($y_s$) at time $t$ The values of stress indicator metric are computed, at 522, based on the equation $S=(A-10B)/T-0.5$, where A represents rewards for persistence and B represents penalties for indecision. Herein, $-1<=S<0.5$. A, B and S are shown in FIG. 8A. The factor of 10 is introduced to increase penalty on indecisive movements. Some possible gameplays and the corresponding values of S are shown in FIGS. 8B to 8E.

Figure 9:
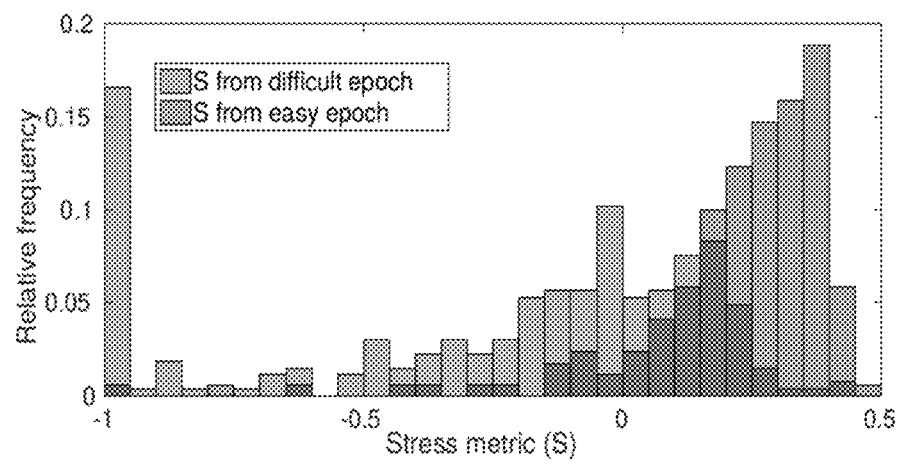
FIG. 9 illustrates histogram showing distribution of values of S from epochs of easy and difficult versions of the game in accordance with some embodiments of the present disclosure.

Herein, each epoch of gameplay yielded a single value of S, along with a single feature vector derived from the EEG signals of that epoch. All feature vectors from every epoch of every subject (total 443 epochs from 22 subjects) were used to rank features using a wrapper method. The distribution of all values of S is shown in FIG. 9.

Figure 10A:
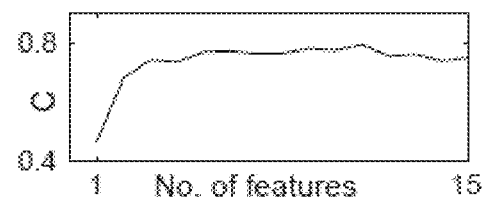
FIGS. 10A, 10B and 10C show the performance for a single subject in accordance with some embodiments of the present disclosure.
Figure 10B:
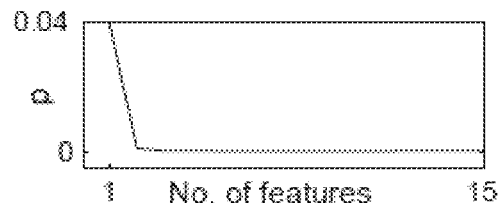
Figure 10C:
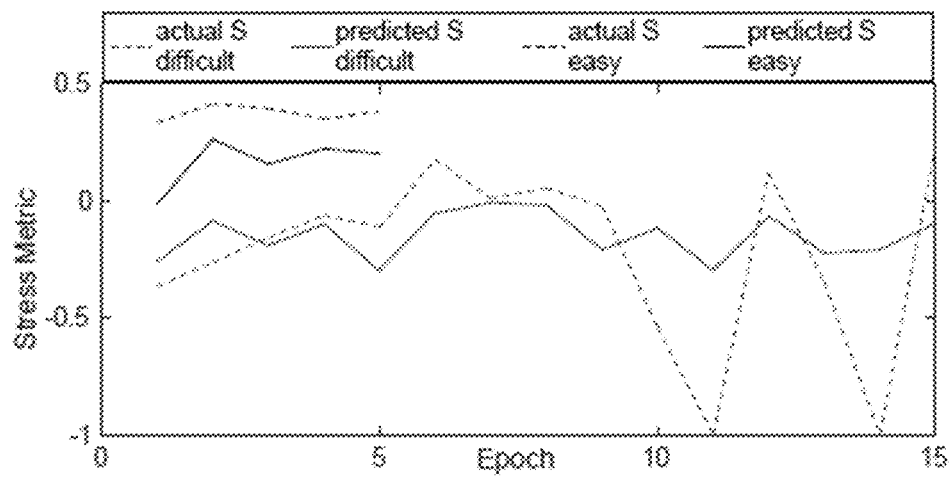

FIGS. 10A, 10B and 10C show the performance for a single subject, in accordance with an example embodiment of the present disclosure. A random forest is trained as a regressor and evaluated on all epochs of a single subject using LOOCV with respect to epochs. Correlation coefficient and p-value between the actual value of S and the predicted value for a single subject are plotted in FIGS. 9A and 9B for the top 1 to 15 features. It can be observed that for 3 or more features, C>0.73 and p<<0.05. The subject had 5 epochs in the easy version and 15 in the difficult version of the game. The regression model trained on 19 out of 20 epochs and tested on the remaining epoch in turn using the top 15 features. Values of the predicted stress metric (S) are compared to the actual values in FIG. 9C when evaluated using those 15 features. GSR, being a slowly-varying signal, was not used here. GSR properties lagged significantly behind the corresponding changes in keystroke patterns and often the change in GSR for an epoch carried over to the next. This is because, while an epoch lasted for about 10 seconds, changes in GSR were reflected at a lag of about 3 seconds (30%).

Various embodiments disclosed herein provide method and system for classification and quantification of cognitive stress from physiological variables and keystrokes. The disclosed system models a robust model with respect to sensors which is readily deployable, without further training, on any new data available from a new subject. The main contributions of disclosed embodiments include design of a stimulus to induce acute stress. Further, the system identifies features from EEG, GSR and PPG signals that correlate with stress. In addition, the system incorporating feature level and decision level fusion of information from the sensor signals to improve subject-independent stress detection performance. Moreover, the disclosed system analyses keystroke data collected during the experiments to propose a novel stress indicator metric. The system trains a subject-dependent regression model using EEG features to predict said metric.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method for classification and quantitative estimation of cognitive stress in real-time, the method comprising:

obtaining, while a user is engaged in performance of a task, a plurality of non-invasive physiological signals from a plurality of physiological sensors accessible to the user, via one or more hardware processors;

identifying a plurality of feature sets from the plurality of non-invasive physiological signals, via the one or more hardware processors, the plurality of feature sets correlating with the cognitive stress experienced by the user while engaging in the performance of the task; and predicting, using a regression model, a stress indicator metric comprising a quantitative estimate of the cognitive stress experienced by the user during the performance of the task, via the one or more hardware processors, wherein, the regression model is trained using the plurality of feature sets, and independently determined quantitative estimates of cognitive stress used as a ground truth to output value of the stress indicator metric, and wherein, the ground truth is determined from keystroke data associated with the performance of keyboard-based tasks comprising navigation of one or more moving objects to at least one target from a plurality of targets.

2. The method of claim 1, wherein the plurality of non-invasive physiological signals comprises Electroencephalogram (EEG) signal to estimate the neural responses of the user, Photoplethysmogram (PPG) to analyze cardiac parameters of the user, and Electrodermal or Galvanic Skin Response (GSR) to determine changes due to variations in skin conductance of the user, in real-time.

3. The method of claim 2, wherein identifying the plurality of feature sets from the plurality of non-invasive physiological signals comprises:

extracting a feature set individually from each non-invasive physiological signal of the plurality of non-invasive signals to obtain the plurality of feature sets; and performing feature reduction on each feature set of the plurality of feature sets to obtain an optimum feature set.

4. The method of claim 1, further comprising preprocessing the plurality of non-invasive physiological signals in order to reduce corruption of the plurality of non-invasive physiological by noise, reduce intra-user and inter-user variability and decrease computational effort for identifying the plurality of feature steps and predicting the stress indicator metric.

5. The method of claim 1, wherein determining the quantitative estimate of the cognitive stress from the keystrokes comprises:

obtaining the keystroke data during performance of at least one keyboard-based task involving navigating a moving object to a target object out of a plurality of target objects;

determining relative position of the moving object with respect to the ultimate target object during each epoch of the keyboard based task, an epoch associated with the moving object comprises a duration of time available for directing said moving object to the target object, the relative position determined in terms of keystrokes ($y_s$) made during the performance of keystroke based task in a direction towards the target object and keystrokes ($y_o$) away in a direction away from the target object, such that relative position of the target object is $x=y_s-y_o$;

defining for each of the epochs during the keyboard-based task a single value of f(t) at each time instant (t=0 to T, T=duration of epoch) timestamp is logged such that:

$f(t)=f(t-1)$ denotes no keystroke at time $t$ $f(t)=f(t-1)-1/x$ denotes single keystroke in opposite direction (yo) at time $t$ $f(t)=f(t-1)+1/x$ denotes single keystroke in same direction (ys) at time $t$ computing the values of stress indicator metric based on the equation
S=(A−10B)/T−0.5, where, where A represents rewards for persistence and B represents penalties for indecision, and $A=\Sigma_{t=0}^{T}\min[f(T),\max\{f(t),f(0)\}]$ $B=\Sigma_{t=0}^{T}|\min\{f(t),f(0)\}|+\max\{f(t),f(T)\}-f(T)$.

6. The method of claim 1, wherein the regression model is trained using plurality of features sets from each non-invasive physiological signal individually or in combination as predictors and the stress indicator metric S as ground truth.

7. The method of claim 1, further comprising developing, from the plurality of non-invasive physiological signals, a classification model to differentiate between high and low cognitive stress experienced by the user.

8. The method of claim 7, wherein developing the classification model comprises:
classifying the level of cognitive stress based on the plurality of feature sets obtained from the plurality of non-invasive physiological signals using a feature level fusion and a decision level fusion,
wherein, the feature level fusion of the plurality of feature sets comprises:
accumulating the feature sets associated with the plurality of non-invasive physiological signals to obtain a composite feature set, and
performing feature reduction of the composite feature set,
and wherein, the decision level fusion comprises:
training a plurality of models individually corresponding to each of the plurality of features set from each non-invasive physiological signals as originating from to classify each of the plurality of non-invasive physiological signals as high stress or low stress task(s), and
applying a logical AND operator to the binary classification outcome of the plurality of non-invasive physiological signals obtained from the individual classifiers.

9. A system for classification and quantitative estimation of cognitive stress in real-time, the system comprising:
one or more memories; and
one or more hardware processors, the one or more memories coupled to the one or more hardware processors, wherein the one or more hardware processors are capable of executing programmed instructions stored in the one or more memories to:
obtain, while a user is engaged in performance of a task, a plurality of non-invasive physiological signals from a plurality of physiological sensors accessible to the user;
identify a plurality of feature sets from the plurality of non-invasive physiological signals, the plurality of feature sets correlating with the cognitive stress experienced by the user while engaging in the performance of the task; and
predict, using a regression model, a stress indicator metric comprising a quantitative estimate of the cognitive stress experienced by the user during the performance of the task,
wherein, the regression model is trained using the plurality of feature sets and independently determined quantitative estimates of cognitive stress used as a ground truth to output the value of the stress indicator metric, and
wherein, the ground truth is determined from keystroke data associated with the performance of keyboard-based tasks comprising navigation of one or more moving objects to at least one target from a plurality of targets.

10. The system of claim 9, wherein the plurality of non-invasive physiological signals comprises Electroencephalogram (EEG) signal to estimate the neural responses of the user, Photoplethysmogram (PPG) to analyze cardiac parameters of the user, and Electrodermal or Galvanic Skin Response (GSR) to determine changes due to variations in skin conductance of the user, in real-time.

11. The system of claim 9, wherein the one or more hardware processors are further configured by the instructions to preprocess the plurality of non-invasive physiological signals in order to reduce corruption of the plurality of non-invasive physiological by noise, reduce intra-user and inter-user variability and decrease computational effort for identifying the plurality of feature steps and predicting the stress indicator metric.

12. The system of claim 11, wherein to identify the plurality of feature sets from the plurality of non-invasive physiological signals, the one or more hardware processors are further configured by the instructions to:
extract a feature set individually from each non-invasive physiological signal of the plurality of non-invasive signals to obtain the plurality of feature sets; and
perform feature reduction on each feature set of the plurality of feature sets to obtain an optimum feature set.

13. The system of claim 9, wherein to determine the quantitative estimate of the cognitive stress from the keystrokes, the one or more hardware processors are further configured by the instructions to:
obtain the keystroke data during performance of at least one keyboard-based task involving navigating a moving object to a target object out of a plurality of target objects;
determine relative position of the moving object with respect to the ultimate target object during each epoch of the keyboard based task, an epoch associated with the moving object comprises a duration of time available for directing said moving object to the target object, the relative position determined in terms of keystrokes (ys) made during the performance of keystroke based task in a direction towards the target object and keystrokes (yo) away in a direction away from the target object, such that relative position of the target object is $x = y_s - y_o;$ define for each of the epochs during the keyboard-based task a single value of f(t) at each time instant (t=0 to T, T=duration of epoch) timestamp is logged such that:

$f(t)=f(t-1)$ denotes no keystroke at time $t$ $f(t)=f(t-1)-1/x$ denotes single keystroke in opposite direction (yo) at time $t$ $f(t)=f(t-1)+1/x$ denotes single keystroke in same direction (ys) at time $t$ compute the values of stress indicator metric based on the equation S=(A−10B)/T−0.5, where, where A represents rewards for persistence and B represents penalties for indecision, $A = \Sigma_{t=0}^{T} \min[f(T), \max\{f(t), f(0)\}]$ $B = \Sigma_{t=0}^{T} |\min\{f(t), f(0)\}| + \max\{f(t), f(T)\} - f(T).$

14. The system of claim 9, wherein the one or more hardware processors are further configured by the instructions to train the regression model using plurality of features sets from each non-invasive physiological signal individually or in combination as predictors and the stress indicator metric S as ground truth.

15. The system of claim 9, wherein the one or more hardware processors are further configured by the instructions to develop, from the plurality of non-invasive physiological signals, a classification model to differentiate between high and low cognitive stress experienced by the user.

16. The system of claim 15, wherein to develop the classification model, the one or more hardware processors are further configured by the instructions to:
classify the level of cognitive stress based on the plurality of feature sets obtained from the plurality of non-invasive physiological signals using a feature level fusion and a decision level fusion,
  wherein, to perform the feature level fusion of the plurality of feature sets, wherein the one or more hardware processors are further configured by the instructions to:
    accumulate the feature sets associated with the plurality of non-invasive physiological signals to obtain a composite feature set, and
    perform feature reduction of the composite feature set,
  and wherein, the decision level fusion comprises:
    train a plurality of models individually corresponding to each of the plurality of features set from each non-invasive physiological signals as originating from to classify each of the plurality of non-invasive physiological signals as high stress or low stress task(s), and
    apply a logical AND operator to the binary classification outcome of the plurality of non-invasive physiological signals obtained from the individual classifiers.

17. A non-transitory computer-readable medium having embodied thereon a computer program for executing a method for classification and quantitative estimation of cognitive stress in real-time, the method comprising:
obtaining, while a user is engaged in performance of a task, a plurality of non-invasive physiological signals from a plurality of physiological sensors accessible to the user, via one or more hardware processors;
identifying a plurality of feature sets from the plurality of non-invasive physiological signals, via the one or more hardware processors, the plurality of feature sets correlating with the cognitive stress experienced by the user while engaging in the performance of the task; and
predicting, using a regression model, a stress indicator metric comprising a quantitative estimate of the cognitive stress experienced by the user during the performance of the task, via the one or more hardware processors,
wherein, the regression model is trained using the plurality of feature sets, and independently determined quantitative estimates of cognitive stress used as a ground truth to output value of the stress indicator metric, and
wherein, the ground truth is determined from keystroke data associated with the performance of keyboard-based tasks comprising navigation of one or more moving objects to at least one target from a plurality of targets.

* * * * *